United States Patent [19]

Furchner et al.

[11] 3,973,927
[45] Aug. 10, 1976

[54] PROCESS AND INSTALLATION FOR CREATING OPTIMUM CLIMATIC CONDITIONS IN A ROOM BY AIR PURIFICATION AND IONIZATION CONTROL

[76] Inventors: Helmut Furchner, Wilhelm-Haspel Strasse, D-7032 Sindelfingen 63, Germany; Bernard Stroiazzo, rue Paul Deroulede, F-54520 Laxou 24, France

[22] Filed: Jan. 20, 1975

[21] Appl. No.: 542,252

[30] Foreign Application Priority Data
Jan. 22, 1974  France ............................ 74.02975

[52] U.S. Cl. ...................................... 55/4; 21/74 R; 55/102; 55/106; 55/135; 55/136; 55/139; 55/150; 55/154; 55/279; 317/262 AE
[51] Int. Cl.² .......................................... B03C 3/68
[58] Field of Search ............ 55/2, 4, 102, 105, 104, 55/106, 122, 124, 128, 135, 136, 138, 279; 137/88; 21/74 R; 128/190; 317/262 AE; 340/248

[56] References Cited
UNITED STATES PATENTS

| | | | |
|---|---|---|---|
| 2,060,842 | 11/1936 | Yaglou | 55/4 |
| 2,576,399 | 11/1951 | Hicks | 21/74 R |
| 3,483,672 | 12/1969 | Jahnke | 55/148 |
| 3,488,675 | 1/1970 | Eishold | 55/105 |
| R27,027 | 1/1971 | Cristofv et al. | 55/4 |

Primary Examiner—Bernard Nozick
Attorney, Agent, or Firm—Robert E. Burns; Emmanuel J. Lobato; Bruce L. Adams

[57] ABSTRACT

The present invention provides a process and apparatus for electro-control of climatic and ion conditions and ion enrichment of air, for establishing optimal climatic conditions in buildings, rooms and enclosures of all kinds.

It establishes a high voltage electrostatic field between ceiling and floor. It regulates the rate of emission of ions, the field and the other parameters.

The present invention has application to air conditioning, agricultural activities, food products and medical activities.

9 Claims, 1 Drawing Figure

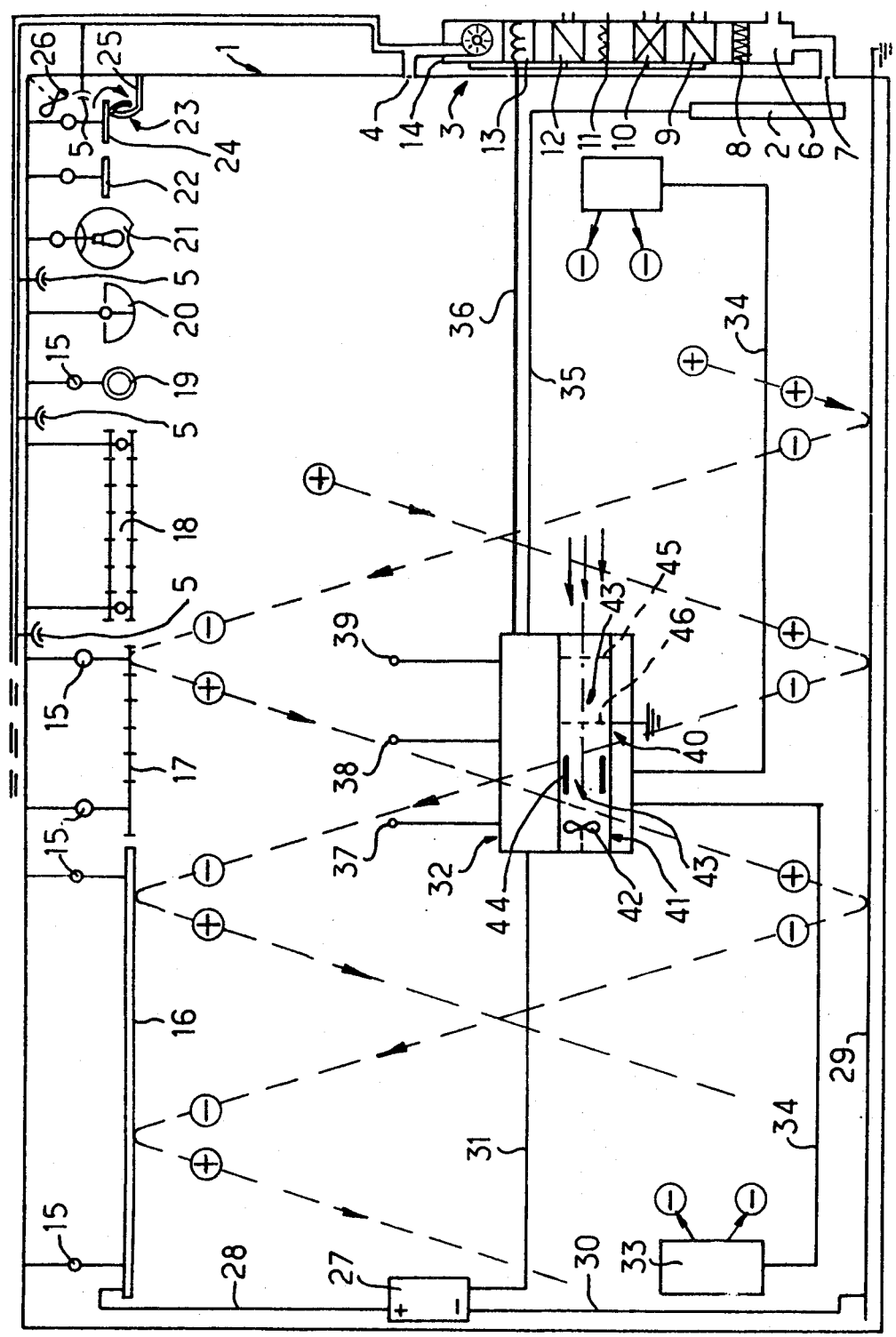

PROCESS AND INSTALLATION FOR CREATING OPTIMUM CLIMATIC CONDITIONS IN A ROOM BY AIR PURIFICATION AND IONIZATION CONTROL

The present invention relates to an electro-air-conditioning process and ionic regulation for the purification and the ionic enrichment of air, and, in a more general way, for the establishment of optimum climatic conditions, in an enclosure such as buildings, rooms and chambers which may be fixed or movable. It concerns the installation to be used, and, in particular, the combination of different apparatus and materials.

The desire of every human being is to feel a certain well-being when he is indoors.

This feeling of well-being becomes increasingly important in the stuffy atmosphere of our large cities. It has been shown that a comfortable environment makes the working easier and increases productivity and quality of work.

It has been proposed that the growth of animals and plants is largely favored by the electric components of air. These facts and the requirements for the purification of air for therapeutic needs have spurred the air-conditioning industries to develop installations for creating climatic conditions in which the atmosphere is aseptic, pure, pleasing and biologically favorable to the growth.

Devices and processes exist for electro-air-conditioning by an electro-static field between the ground and ceiling of movable or fixed closed chambers.

In these processes, the positive pole of an electrostatic high voltage generator is connected to a ceiling electrode and the negative pole to a ground electrode. This system can be integrated into a classical air-conditioning installation and ensure the regulation of certain climatic parameters.

Thus, certain climatic conditions have been controlled such as the temperature of ambient air and its humidity, more or less closely using the high voltage electrostatic generator. The point of working has thus been desired to be compelled to constantly stay in the scope of well-being. But this leads to complex devices and, moreover, their effects are proved insufficient on the climatic level.

In spite of the generation and the control of classical climatic conditions and the establishment of an electric field, it is noted that some people still suffer physically unpleasant feelings such as lack of air, oppression and nervousness because of the influence of the external atmospheric conditions and of the substantially changeable characteristics of the dielectric which is the volume of air between electrodes. It has been thus found, that the regulation of the usual climatic parameters is not sufficient. It is now known that it is necessary to re-create and sustain the beneficial natural ionization inside the rooms and the buildings.

It has been proposed that another important factor exists which contributes to the establishment of an internal healthy and pleasing climate. This is the concentration ratio between the population of small and average negative ions of oxygen and the population of positive ions of oxygen. Indeed, the small ions and contingently the average ions of oxygen ensure breathing catalysis and the value of the aforesaid concentration ratio plays a direct part in the feeling of lack of air. An analogous reasoning can be applied to animals and plants the growth of which is better in the optimum climatic conditions which the present invention creates inside the buildings.

The ventilation openings, the blowing sheaths, the central humidifier, and in a general way, the heating apparatus generate a large quantity of positive ions or collect the negative ions and disturb entirely the relative concentration of the catalytic ions. It therefore becomes necessary to emit small and average negative ions of oxygen, in a quantity sufficient to regulate this ion emission taking account of the other parameters and especially to maintain the negatively charged ions in a suitable volume.

A whole range of generators of negative ions from radioactive substances, negative high voltage discharges, ultraviolet radiation or simply ionized aerosol generators have been built.

Because of their short range, in the region of a meter, these generators can only be used individually and cannot integrate into a complete air-conditioning installation.

Further, their use is dangerous, for the conversion of oxygen into ozone occurs at a rate from 5 to 10%, whereas the maximum relative quantity of ozone in the air which is allowable is only 1/100,000. Further, the result is not uniform, for the number of ions given off declines exponentially with distance from the apparatus.

The invention artificially creates and regulates the optimum climatic conditions met in nature for example at an altitude between 1,000 and 2,000 m. and in places where it is pleasant to live, conditions which are destroyed by the structures in particular those carried out by our modern buildings.

These climatic conditions have been found to be very important for they enhance the biological balance of every cellular organism by activating the dynamic and electrical cellular metabolism and the asepticization of all the ambient surroundings polluted by micro-organisms.

The process and apparatus of the present invention create and control an electrostatic vertical field and re-establish the ionic balance of oxygen ions in the ambient air, control and regulate the principal factors on which the climatic conditions depend to make the internal climate of a building independent from the characteristics, influences and fluctuations of the external climate.

The process according to the present invention is characterized in that there is provided, in a building with or without heating and air conditioning an almost constant, vertical, electrostatic field between the floor and ceiling, with a positive pole connected to one or several ceiling electrodes; small and medium negative oxygen ions are emitted and controlled in one or several locations in said enclosure in sufficient numbers and at an average initial velocity to generate an ionic convection current in the electrostatic field; and by an ionic injection there is provided a population equilibrium for erecting optimum climatic conditions, by particular regulating the ionic emission and the strength of the electrostatic field by field, relative humidity and temperature, by suitable data from the sensing means with a co-ordinating device for regulating the generators of the electrostatic field of negative ions, so as to maintain the following parameters in the enclosures:

a ground resistance of from $10^9$ to $10^{11}$ ohm centimeter;

an electrostatic field value of from 500 to 2000 volt/meter;

a ratio of local, large and small positive ion and negative ion populations of from 0.7 to 1.3 as N+/N−;

and in a particular embodiment of the process of the present invention for air conditioning the criteria for the well-being for an average man are:

a temperature between 18° and 23°C., a relative humidity between 40 and 50%, and the ionic ratio of 1.3 is never exceeded.

The advantages of the process and of the present apparatus are numerous and some will be given. However, the inventors believe the enumeration is not complete and there are many more particularly in the bacteriostatic and bioelectric fields, in farming and agriculture.

By complete and automatic electro-air-conditioning, the ambient conditions remain optimum and constant whatever the variations of parameters of values representing the inner microclimate and the variations of exterior atmospheric conditions may be.

The invention allows to join together a maximum of benefic therapeutic and useful effects.

The simultaneous presence and regulation of an electrostatic field and ionic emission has the following effects:

natural ionization is favored, avoiding the recombination of the oxygen ions;

artificial ionization is effected by ion convection; and the homogenization and the balance of the ionization are ensured anywhere in the total volume of any enclosure.

Many practical effects result, which include a physiological well-being, a faster and more harmonious growth, a therapeutic effect, air sterilization, and food preservation, as noted at the end of the description.

Air thus becomes more breathable as the small and eventually the average negative ion is a catalyst for the gaseous exchange with the haemoglobin of the blood in the pulmonary cells. By increasing the negative concentration, the gaseous exchange in the lungs is increased and the flow of the blood is improved while reducing the quantity of air, necessary at each inhalation. The feeling of lack of air or of a foul air is totally removed.

As a direct consequence, the rate of air renewal is reduced to 60 to 70% of the number of cubic meters of air, normally necessary per man per hour. As a result, there is a saving in calorific, refrigeration and electrical energy in operating the heating and air conditioning installations.

The effects of the microbial and bacterial purification and the removal of all the germs contained in the enclosure space and the possibility of creating a favorable bio-physiological effect the very same feeling as during a stay at a mean height, have also been noted.

The aforesaid negative ions are by preference small and average negative ions of oxygen.

The present invention will be understood from the following non-limiting description, illustrated by the accompanying drawing, the sole FIGURE of which is a schematic view of an assembly for use in the process of the present invention, with indication of the ion convection.

The negative ions created according to the invention are preferably small and medium oxygen ions.

A complete and careful study of conditions, parameters and physical factors necessary to obtain ideal electro-air-conditioning has determined the important parameters the variation of which significantly alters the atmosphere of an enclosure, and the amplitude of variation and their relative influence on the well-being of persons.

These parameters have to stay within the following ranges for comfortable air-conditioning and for selected physiological conditions:

a. establishment of an electrostatic field between ceiling and ground from 500 to 2000 volts/meter;

b. ratio of relative concentration between positive ions and negative ions betweens 0.70 and 1, the figure 1.30 not being exceeded in any event;

c. surface insulation of the ground between $10^9$ and $10^{11}$ ohms-cm.

In addition to the electrostatic field between ground and ceiling, it is necessary to establish and to regulate a sustained flow of small and average ions of oxygen of negative polarity, from one or more generators of ions.

The simultaneous presence of an electrostatic field and of one or more flows of small and average negative ions of oxygen and their regulation allow a balance of the ionic population and an ionic self-sustained convection current in normal operation.

After setting forth the variations in the ranges of the parameters with direct and significant influence on the atmosphere of a room the installation for achieving this will be described as well as the process of creating these optimum climatic conditions.

As to the process:

Inside a room provided for example with a complete heating or air-conditioning system, including hot and-/or cold air generators as well as a humidifier-dehydrator, or without any heating and/or air-conditioning equipment, a high voltage electrostatic field is established between floor and ceiling for a high voltage electrostatic generator with the positive pole of the generator connected to ceiling electrodes and the negative pole of the generator to floor electrodes; then in one or more locations in the room one or more fluxes are emitted which fluxes have small and medium negative oxygen ions with adjustable intensity and an average initial velocity.

The intensity of these negative ion fluxes and other values, especially that of the electrostatic field are adjusted by means of sensors, through a co-ordinating device which controls the ion and electrostatic field generators, so as to maintain these values within the range indicated above.

To ensure the establishment of this electrostatic field the floor conductivity must be comprised between $10^9$ and $10^{11}$ ohms-cm.

As to the apparatus, which is very schematically shown in the drawings:

Enclosure 1 has no heating or air-conditioning system or is simply heated by stationary heating elements 2 or is provided with an air-conditioning system 3 feeding the room with conditioned air through lateral openings 4 or upper openings 5. This assembly comprises a lower air inlet compartment 6, extracting fresh air from outside and supplying air to the room through opening 7. This air-conditioning assembly is provided with a series of compartments including a filter 8, hot unit 9, cold unit 10, humidifier 11, hot unit 12, dehydrator 13 and a blowing unit 14 for injecting conditioned air into enclosure 1.

It is in enclosure or room 1 which may either be provided with a conventional heating system or have no such system, that the optimal electro-air-conditioning system of the present invention may be installed.

The system comprises ceiling electrodes, preferably made of metal, which are connected to the ceiling by means of insulators 15. These electrodes may be in an insulating support fastened directly onto the ceiling or forming a false ceiling.

These electrodes may have a variety of shapes including flat electrodes 16, single grid-shaped electrodes 17 or double grid-shaped electrodes 18 for the direct purification of air for contaminants such as smoke, germs, odors and dust; tube-shaped electrodes 19, semi-cylindrical electrodes 20, electrodes accommodated in a lamp 21, a single small plate electrode 22 or a compound electrode 23. The compound electrode 23 comprises a flat and straight electrode 24 located adjacent to earthed points 25 to produce negative ions by point effect or by means of radio-elements, the compound electrode 23 being located in front of a fan 26 which blows ions into the used volume of the room or enclosure 1.

A high voltage electrostatic generator 27 of range 500 – 10,000 volts is connected to the ceiling electrodes through cable 28 and to floor electrodes 29 through cable 30, electrodes 29 being earthed. The positive pole of the generator 27 is connected to the ceiling electrodes, the negative pole being connected to floor electrodes 29.

Electric connection 31 connects generator 27 to a coordinating device 32 which controls its operating parameters in relation to the variations of other parameters, especially those of the electric field and of the ion population.

One or more generators of small and medium oxygen negative ions 33, are installed in the enclosure for example suitably near or inside air-conditioning openings 4 or 5 and are connected to the central co-ordinating device by lines 34. The stationary heating elements 2 are connected to the central co-ordinating device by electric line 35 for control thereof. The components of the air conditioning unit are linked to the central co-ordinating device through a multiline connection 36 for control.

The co-ordinating device makes it possible to regulate all air-conditioning parameters and especially electric field and ion population parameters in relation to the variations of other parameters for keeping at all times optimal climatic conditions.

For this purpose the co-ordinating device is connected to sensors 37, 38, 39 and 40 which are specifically sensitive to temperature, relative humidity, pressure and relative population of negative and positive ions.

The compound sensor 40 is essential, whereas the specific sensors 37, 38 and 39 may be eliminated.

The sensors may be duplicated or triplicated and are located in appropriate places for ensuring a good overall regulation.

The co-ordinating device 32 controls all data supplied by the sensors and acts on the generators to ensure the automatic regulation of the parameters, individually, collectively or correlatively.

A simplified co-ordinating device which is technically easier to fabricate may only be connected to compound sensor 40 and act only, for example by servocontrol, on the electrostatic field and negative ions generators.

The collection of data concerning the electric field and the ion concentration and the servocontrol of electric field and ion generators depend on two distinct electronic channels with a common component.

The coordinating device may comprise several collecting and controlling channels to air-condition several enclosures as for example all the rooms of a house. This would be a "central" coordinating device.

Compound sensor 40 for measuring the electronic field and the ion concentration is formed, for example, of a tube 41 in which a constant air flow is maintained by blower 42. This tube contains a flat air capacitor 43 with an upper positive electrode 44. The air flow is the dielectric of the capacitor. A terminal grid electrode 45, extending across the whole section of the tube measures unipolar ion concentrations; these ions may be negative. A neutralizing electrode 46 of the same type as electrode 45 is earthed and is located in front of the capacitor 43.

Because of the simultaneous presence of an electrostatic field between the floor and the ceiling and of negative ions produced in a controlled way by the generators, an ionic equilibrium is established in the room in relation with the desired regulation. An ionic convection current is also formed.

This effect contributes to the ionic equilibrium beyond the automatic regulation achieved artificially by the injection of negative ions.

This process of the present invention has many applications as can be seen in the following description as to what the electric field can do by itself or in combination with ion fluxes.

It will bring about the precipitation of dust especially at the positive pole;

It will eliminate smoke and odors without any need to renew the ambient air;

It will sterilize ambient air by destroying microorganisms and viruses which will be precipitated either into the positive pole (ceiling) or into the negative pole (floor) according to their polarity. In order to facilitate this precipitation, enough negative ions are emitted to polarize microorganisms to a maximum extent;

It will give rise to a convection of oxygen ions and molecules. Beyond a certain ion population limit, this convection is practically self-sustained and this is why ions must be injected in one or several spots;

It will increase the life of naturally occurring ions formed by ionizing radiations, continuously crossing the atmosphere, which ions may come from the ground, the building materials, radio-active gases in the air, or in the universe, or which result from plant photosynthesis. It will obviously also increase the life of artificially formed ions;

It will help plants grow because it facilitates the rising of sap therein.

Sap is carried along by solvated (water dissolved) electrons which pass upwardly in plants. The establishment of an electric field in greenhouses makes it possible to activate the growth of plants, to eliminate insects and to destroy moulds. This process eliminates the use of products harmful for human beings in the treatment of vegetables grown in hothouses.

We claim:

1. A process for electrically establishing optimal climatic conditions and for ionizing and purifying the air in a building, room or enclosure, characterized by establishing, with or without air conditioning or heating an adjustable, vertical electrostatic field between the floor and ceiling of said enclosure by means of a high voltage electrostatic field generator having one pole thereof connected to at least one ceiling electrode and the other pole thereof to the floor, causing small and medium negative oxygen ions to be emitted from a negative oxygen ion generator in one or several locations in sufficient numbers and at an average initial velocity to generate an ionic convection current in the electrostatic field and provide an ionic population equilibrium and selective climatic conditions, sensing the strength of the electrostatic field and the ionic concentration in the enclosure by means of sensing means, continuously feeding data from the sensing means to a co-ordinating device and regulating the strength of the electrostatic field generated by said electrostatic field generator and the rate of emission of said negative ions from said negative ion generator by means of said coordinating device so as to maintain the following parameters in the enclosure:

an electrostatic field volume of from 500 to 2000 volts/meter.

a ratio of small and average positive ions to negative oxygen ions in the room of from 0.7 to 1.3, and a ground resistance of from $10^9$ to $10^{11}$ ohm - centimeter.

2. A process as claimed in claim 1 in which the ratio of 1.3 is never exceeded, the temperature in the enclosure is maintained at from 18° to 23°C., and the relative humidity is maintained at from 40% to 50%.

3. A process as claimed in claim 1 in which additional negative ions are emitted into the enclosure by means of a blower behind a compound electrode formed by a small plate insulated form and mounted in the ceiling which plate is located adjacent at least one point, an electrostatic field being established between the plate and the point to produce negative ions.

4. A process as claimed in claim 1 in which the coordinating device regulates the parameters individually, collectively, or correlatively.

5. An electroclimatic assembly for establishing optimal conditions, which assembly comprises a high voltage electrostatic generator 27 having one pole thereof connected to at least one ceiling electrode, and the other pole thereof connected to at least one floor electrode, at least one negative ion generator 33 located in the enclosure for emitting negative ions in at least one location in the enclosure, and a coordinating device 32 connected to and operative to automatically regulate said generators whereby said assembly may operate continuously at the level required for an ideal climate in the enclosure, with or without an air conditioning plant 3.

6. An assembly as claimed in claim 5 in which the positive pole of the generator is connected to the ceiling electrodes and the negative pole of the generator to the floor electrode.

7. An assembly as claimed in claim 5 including sensing means 37, 38, 39, 40 for sensing the temperature, relative humidity, pressure, the negative ion concentration and the strength of the electrostatic field and controlling the respective generators.

8. An assembly as claimed in claim 7 in which the sensing means 40 includes a plurality of sensors operative to sense the electrostatic field strength, and ion concentration in the enclosure and each being connected to the coordinating device which coordinating device is connected to the generators to be regulated.

9. An assembly as claimed in claim 7 in which the coordinating device comprises a compound sensor 40 and at least two amplification units for data supplied by said compound sensor and two cervial contral units whereby said coordinating device is operative to collect the data of field strength and ion concentration.

* * * * *